(12) United States Patent
Kramer et al.

(10) Patent No.: US 11,051,967 B2
(45) Date of Patent: Jul. 6, 2021

(54) FUNCTIONAL FRACTURE BRACE FOR FEMUR FRACTURES

(71) Applicant: DF2, LLC, Highland Park, IL (US)

(72) Inventors: Andrea Kramer, Highland Park, IL (US); David Speers, Schaumburg, IL (US)

(73) Assignee: DF2, LLC, Highland Park, IL (US)

( * ) Notice: Subject to any disclaimer, the term of this patent is extended or adjusted under 35 U.S.C. 154(b) by 356 days.

(21) Appl. No.: 15/726,745

(22) Filed: Oct. 6, 2017

(65) Prior Publication Data

US 2018/0098873 A1   Apr. 12, 2018

Related U.S. Application Data

(60) Provisional application No. 62/405,486, filed on Oct. 7, 2016.

(51) Int. Cl.
*A61F 5/058* (2006.01)
*A61F 5/01* (2006.01)
(Continued)

(52) U.S. Cl.
CPC .......... *A61F 5/0585* (2013.01); *A61B 5/0064* (2013.01); *A61B 5/1072* (2013.01);
(Continued)

(58) Field of Classification Search
CPC .. A61F 5/0585; A61F 5/0193; A61F 5/05841; A61B 90/39; A61B 5/0064;
(Continued)

(56) References Cited

U.S. PATENT DOCUMENTS

| 5,915,386 A | * | 6/1999 | Lloyd | A61B 5/1077 128/897 |
| 6,558,606 B1 | | 5/2003 | Kulkarni et al. | |

(Continued)

FOREIGN PATENT DOCUMENTS

| KR | 2011-0097822 A | * | 8/2011 | G06F 17/50 |
| WO | WO 2010/054341 A1 | * | 5/2010 | G06F 19/00 |
| WO | WO-2010054341 A1 | * | 5/2010 | B33Y 80/00 |

OTHER PUBLICATIONS

Rakesh John, Current Concepts in Paediatric Femoral Shaft Fractures, 2017, The Open Orthopaedics Journal, vol. 11, pp. 1-10 (Year: 2017).*

(Continued)

*Primary Examiner* — Rachael E Bredefeld
*Assistant Examiner* — Trisha Talapatra
(74) *Attorney, Agent, or Firm* — John V. Daniluck; Gerald W. Roberts; Dentons Bingham Greenebaum LLP (57) ABSTRACT

A process for treating femoral fractures in children includes diagnosing a patient with a femoral shaft fracture and enclosing the affected limb in a splint. The process further includes scanning the unaffected limb with a three-dimensional scanner and obtaining measurements of the unaffected limb that may be used to form a brace for the affected limb. In addition, the process includes fabricating an orthosis to support the affected limb based on the scan and measurements taken of the unaffected limb, and applying the orthosis to the affected limb.

1 Claim, 4 Drawing Sheets

(51) Int. Cl.
*A61B 90/00* (2016.01)
*A61B 5/107* (2006.01)
*A61B 5/00* (2006.01)
*B33Y 50/00* (2015.01)
*B33Y 10/00* (2015.01)
*B33Y 80/00* (2015.01)

(52) U.S. Cl.
CPC .............. *A61B 5/1079* (2013.01); *A61B 5/48* (2013.01); *A61B 90/39* (2016.02); *A61F 5/0193* (2013.01); *A61B 5/4504* (2013.01); *A61B 2090/3937* (2016.02); *A61B 2090/3983* (2016.02); *B33Y 10/00* (2014.12); *B33Y 50/00* (2014.12); *B33Y 80/00* (2014.12)

(58) Field of Classification Search
CPC . A61B 5/1079; A61B 5/48; A61B 2090/3983; A61B 5/1077; A62B 5/1072; G06T 7/60
USPC ................................................. 602/5, 16, 23
See application file for complete search history.

(56) References Cited

U.S. PATENT DOCUMENTS

| | | | |
|---|---|---|---|
| 6,725,118 B1 * | 4/2004 | Fried ....................... | A61F 5/058 700/118 |
| 6,797,351 B2 | 9/2004 | Kulkarni et al. | |
| 7,332,537 B2 | 2/2008 | Bredt et al. | |
| 7,918,812 B2 * | 4/2011 | Knecht ................. | A61F 5/0123 128/888 |
| 8,417,487 B2 | 4/2013 | Summit et al. | |
| 8,613,716 B2 | 12/2013 | Summit et al. | |
| 8,986,234 B2 | 3/2015 | Summit et al. | |
| 9,168,328 B2 | 10/2015 | Sun et al. | |
| 9,456,901 B2 | 10/2016 | Jones et al. | |
| 9,529,941 B2 | 12/2016 | Summit et al. | |
| 9,532,917 B2 | 1/2017 | Summit et al. | |
| 9,549,837 B2 | 1/2017 | Summit et al. | |
| 9,782,274 B2 | 10/2017 | Summit et al. | |
| 9,858,359 B2 | 1/2018 | Summit et al. | |
| 9,918,866 B2 | 3/2018 | Summit et al. | |
| 10,010,433 B2 | 7/2018 | Layman et al. | |
| 10,231,862 B2 | 3/2019 | Summit et al. | |
| 10,238,520 B2 | 3/2019 | Summit et al. | |
| 10,327,940 B2 | 6/2019 | Summit et al. | |
| 10,398,559 B2 | 9/2019 | Jones et al. | |
| 10,470,914 B2 | 11/2019 | Powell et al. | |
| 10,479,028 B2 | 11/2019 | Zukoski et al. | |
| 10,482,187 B2 | 11/2019 | Summit et al. | |
| 10,716,673 B2 | 7/2020 | Jones et al. | |
| 10,740,857 B2 * | 8/2020 | Tuttle ..................... | A61F 2/5046 |
| 10,779,961 B2 * | 9/2020 | Taylor .................... | A61F 2/5044 |
| 2004/0054307 A1 * | 3/2004 | Mason ................... | A61F 5/0125 602/16 |
| 2004/0068337 A1 * | 4/2004 | Watson .................... | A61F 5/01 700/98 |
| 2007/0133850 A1 * | 6/2007 | Paez ........................ | A61F 5/01 382/128 |
| 2007/0225630 A1 * | 9/2007 | Wyatt ................... | A61F 5/0118 602/21 |
| 2008/0145639 A1 | 6/2008 | Sun et al. | |
| 2010/0138193 A1 * | 6/2010 | Summit ................. | B33Y 50/00 703/1 |
| 2013/0282141 A1 | 10/2013 | Herr et al. | |
| 2013/0296754 A1 * | 11/2013 | Campbell ............. | A61F 5/3761 602/16 |
| 2015/0142150 A1 | 5/2015 | Layman et al. | |
| 2015/0257966 A1 | 9/2015 | Summit et al. | |
| 2016/0213320 A1 * | 7/2016 | Shabah ................... | B29C 64/00 |
| 2017/0246013 A1 | 8/2017 | Erenstone | |
| 2017/0360578 A1 * | 12/2017 | Shin ........................ | B33Y 30/00 |
| 2018/0049906 A1 * | 2/2018 | Janzing .................. | G16H 50/50 |
| 2019/0021634 A1 * | 1/2019 | Morris .................... | A61B 5/742 |
| 2019/0117156 A1 * | 4/2019 | Howard ............... | A61B 5/0024 |
| 2019/0254842 A1 * | 8/2019 | Lunau ................... | A61F 5/0106 |
| 2019/0336042 A1 * | 11/2019 | Lundy ................... | A61B 5/1077 |

OTHER PUBLICATIONS

Vision Quest Industries Incorporated Dba Vq Orthocare; Patent Application Titled "Measurement And Ordering System For Orthotic Devices" Published Online (USPTO 20190254842), 2019, NewsRx LLC, Computer Weekly News, all pages (Year: 2019).*
STIC generated list of patents (Year: 2020).*
STIC generated list of NPL (Year: 2020).*
Bespoke Prosthetic Fairings: The Art of Personalized Medicine with Industrial 3D Printing: https://www.3dsystems.com/learning-center/case-studies/bespoke-prosthetic-fairings-art-personalized-medicine#:~:text=Bespoke%20Prosthetic%20Fairings&3A%20The%20Art%20of%20Personalized%20Medicine,thread%20ties%20Bespoke%E2%80%99s%20philosophy%2C%20work%2C%20goals%20and%20methods., 4 pages, retrieved as early as Jul. 10, 2020.
Maple Leaf by Becker: https://www.beckerorthopedic.com/Product/PrefabricatedOrthoses/Hip/146, 1 page, retrieved as early as Jun. 19, 2020.
Newport, Junior by Orthomerica: https://www.orthomerica.com/products/newport/newport-jr/, 10 pages, retrieved as early as Jun. 19, 2020.
Lil' Hip Hugger by Bolt Systems: https://opedge.com/Articles/ViewArticle/news_2005-01-04_02, 2 pages, retrieved as early as Jun. 9, 2020.
What is Additive Manufacturing: https://www.ge.com/additive/additive-manufacturing, 14 pages, retrieved as early as Jul. 9, 2020.
News Release—3D Systems Acquires Bespoke Innovations: https://www.3dsystems.com/press-releases/3d-systems-acquires-bespoke-innovations, 3 pages, retrieved as early as Jun. 27, 2020.
3D Systems—Go Digital, Stay Agile, Virtual Event Jul. 8, 2020—https://virtualtradeshow.3dsystems.com/, 5 pages, retrieved as early as Jun. 27, 2020.
Bio for Paul K. Tomita—www.st-ip.com/paul-k-tomita.html, 2 pages, retrieved as early as Jun. 27, 2020.
Amendment and Response to Final Office Action dated Oct. 1, 2014 in U.S. Appl. No. 12/823,512, 8 pages, dated Oct. 7, 2014.
Amendment and Response to Non-Final Office Action dated Mar. 11, 2014 in U.S. Appl. No. 12/823,512, 12 pages, dated Jun. 3, 2014.
Amendment and Response to Final Office Action dated May 3, 2013 in U.S. Appl. No. 12/823,512, 10 pages, dated Aug. 5, 2013.
Amendment and Response to Non-Final Office Action dated Sep. 13, 2012 in U.S. Appl. No. 12/823,512, 10 pages, dated Dec. 13, 2012.

* cited by examiner

FUNCTIONAL FRACTURE BRACE FOR FEMUR FRACTURES

BACKGROUND

Pediatric femur fractures account for approximately 2% of all pediatric fractures. They are the most common pediatric fracture, most common pediatric orthopedic injury, and the most common fracture requiring hospital admission. The annual incidence of this injury is approximately 20 per 100,000 children in the United States, and they comprise 21.7% of hospitalized orthopedic trauma, making them one of the most expensive injuries to treat in childhood.

Treatment options for femur fractures vary according to age. Historically, the treatment has evolved from traction and delayed spica casting after traction, to immediate spica casting and even spica casting in the emergency room.

Currently, spica casting is the standard for treatment of diaphyseal femoral fractures in pediatric patients aged 0 to 5 years. However, there are many disadvantages to spica casting. Spica casting requires general anesthesia, is cumbersome for parents and patients, and is difficult to keep clean and maintain. Additionally, a second application of casts is at times necessary when there is progressive malalignment or significant soilage.

SUMMARY

In accordance with an illustrative embodiment, a process for treating femoral fractures in children includes diagnosing a patient with a femoral shaft fracture of an affected limb and temporarily enclosing the affected limb in a splint. The process further includes scanning the patient's unaffected limb with a three-dimensional scanner and taking measurements of the affected limb to obtain brace measurements for use in fabricating an orthosis. Additionally, the process includes fabricating an orthosis to support the affected limb based on the scan of the unaffected limb, and applying the orthosis to the affected limb.

DETAILED DESCRIPTION

An alternative to spica casting, the present disclosure relates to a process for treating femur fractures in children with femoral fracture bracing. Femoral fracture bracing, a type of functional bracing, provides constant, adjustable compression over the fracture, and is more cost effective than spica casting for the treatment of diaphyseal femoral fractures in this age group. Femur functional bracing eliminates the need for an in-patient hospital stay and the risk of general anesthesia. With respect to pediatric femoral shaft fractures, femoral fracture bracing provides the following benefits: (1) simplified treatment; (2) definitive treatment; (3) no anatomical reduction; (4) restoration of linear and rotational alignment; (5) flexibility for remodeling; and (6) immobilization.

In the present disclosure, a femoral fracture brace, or orthoses, is disclosed that is a customized, lightweight, removable brace that can be applied without general anesthesia. The femoral fracture brace provides constant, adjustable compression over a diaphyseal femur fracture. The treatment process includes evaluation, body surface scanning, and fabrication of a brace/orthoses. The femoral fracture brace is a reasonable alternative to a spica cast for non-operative treatment of closed diaphyseal femoral fractures in the 2 month to 5-year-old age group. The femoral fracture brace provides adequate fracture immobilization, cost savings, and improved patient satisfaction. The pediatric femoral fracture brace is made up of different types of high temperature thermoplastics, with anterior panels over the thigh and calf areas and straps to provide the desired compression. Flexibility of the thigh/calf portion and the separate anterior panels allow the brace to maintain constant compression, especially over the fracture, as the size of the thigh changes.

Spica casting has been the conventional standard of care, and provides for circumferential immobilization, control of joints proximal and distal to the fracture, and customization to the size of the patient. Spica casting also provides adjustment of degree of desired limb abduction/flexion to best align the fragments, and by immobilizing the ipsilateral knee, confers some degree of rotational control and correction. However, spica casting is associated with skin and soft tissue complications, necessitates inpatient admission, and may require general anesthesia and the use of an operating theater suite. Further, angular correction and fit-molding in spica casting is only possible before the casting material sets. Later corrections are possible with wedges and blocks but this entails cutting the cast, which (if dealing with small children) may be a traumatic experience for all involved. From a social perspective, patients in spica casts will encounter difficulties with transportation (car seats and strollers), and daily toileting.

Femoral fracture bracing has many of the positive attributes of spica casting, and some additional benefits. Femoral fracture bracing is lighter than a construct of similar dimensions fashioned from Plaster-of-Paris or fiberglass (used in spica casting). Femoral fracture bracing also allows on-the-spot adjustments to compensate for changes in limb size and swelling, and can realign fragment position similar to cast wedges and blocks (but without the magnitude of difficulty associated with using wedges and blocks with spica casting). Placing the femoral fracture bracing in neutral hip flexion can allow for progressive weight-bearing and fracture dynamization. The bracing is also removable, which allows for usage of the toilet and provides parent access for skin care and monitoring.

The present disclosure describes an illustrative process for treating a pediatric femoral fracture by (1) diagnosing a patient with a femoral shaft fracture of an affected limb; (2) enclosing the affected limb in a splint; (3) scanning the patient's unaffected limb with a three-dimensional scanner to obtain brace measurements, or separately obtaining measurements of the unaffected limb; and (4) using an additive manufacturing technique to fabricate a brace based on the obtained brace measurements.

Figure 1:
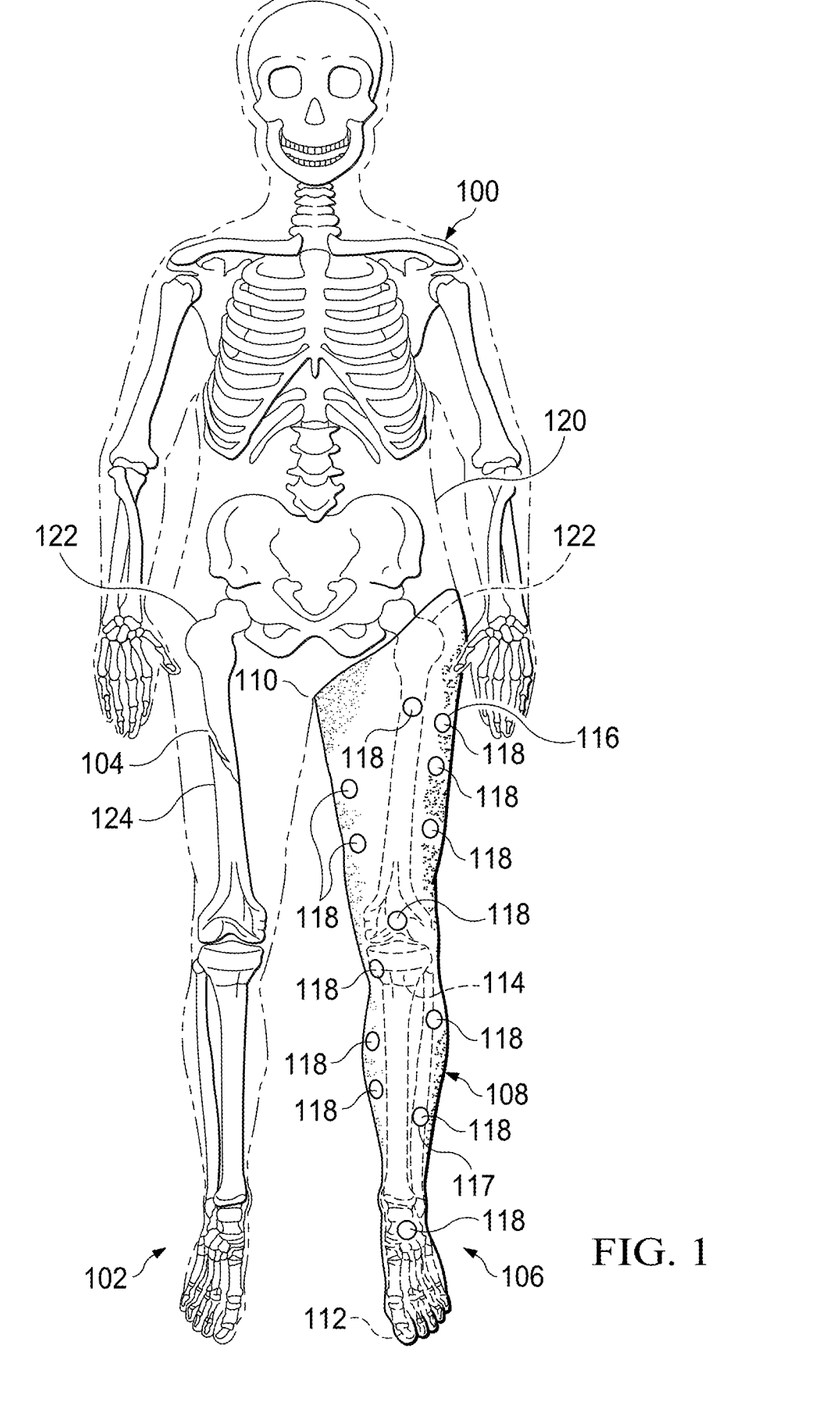
FIG. 1. is a schematic representation of a patient's body.

A representative patient body 100 is shown in FIG. 1. A pediatric femur fracture 104 is usually very painful for a child and can be traumatic to all family members. Traditionally, custom molded orthoses have been fabricated to treat such injuries by casting an involved or affected limb 102 (i.e., the limb having the femur fracture 104) to create a positive model of the affected anatomy, which is then used to make an orthosis. In accordance with an illustrative embodiment, however, three dimensional (3D) scanning is utilized to make an orthosis, making the process to fabricate the orthosis, or brace, less invasive.

Most often, the first encounter between the orthotist and the patient takes place after the patient's affected limb 102 (the limb having a femur 124 with a femur fracture 104) has been put in a hard splint with a flexible over wrap applied. The over wrap usually goes around the waist and over the hard splint down to the foot of the affected limb 102. Removal of the splint and manipulation of the affected limb 102 may be very painful for the patient at this stage in the treatment process. Working with the unaffected limb 106, however, may be less painful.

In an illustrative embodiment of the present disclosure, a process for fabricating an orthosis includes scanning the patient's unaffected limb 106. To obtain the scan of the unaffected limb 106, pain or sedative medications may be used to keep the child patient comfortable and still. An appropriate amount of Valium, or an equivalent medication, for example, may be used to sedate and reduce movement of the patient. A three-dimensional scan may then be obtained while the patient is relatively immobile.

The procedure includes applying a thin stocking 108 over the unaffected limb 106 from the patient's perineum 110 to the end of their toes 112. Landmarks 118 may be positioned at the knee center 114, brace superior end 116, and brace inferior end 117. The landmarks 118 may be drawn with a marker or other suitable technique to ensure that the landmarks 118 are visible on the scan. The landmarks 118 help to define the finished ends of the brace, and the landmark 118 at the knee center 114 may define a reference point from which length measurements may be taken.

A series of circumference, medial/lateral (side to side), and length measurements are taken over the thin stocking 108 of the unaffected limb 106. In some embodiments, the thin stocking 108 may be pre-marked with landmarks 118 or a grid to facilitate measurements. These measurements are then increased by a pre-derived formula (e.g., the application of a swelling factor, which may be applied as a function of distance from the fracture) in order to account for the swelling that is present in the affected limb 102 where the brace will be applied.

Circumferential and medial/lateral measurements are also taken at the waist 120 and hip 122 since the brace does encompass these areas as well. These measurements are not subject to the pre-derived increases, as swelling is usually not an issue in these areas.

The scan may be a three-dimensional scan of the unaffected limb 106, taken with the assistance of a person holding the unaffected limb 106 in the air by flexing the hip 122 so a 360° scan can be obtained. Most often, a series of scans are obtained in order to generate a sufficiently detailed three-dimensional model of the patient's lower torso and the unaffected limb 106.

The scan of the unaffected limb 106 may then be flipped to create a model of the affected limb 102. Using the measurements, pre-derived increased measurements, and flipped image, an orthosis may now be fabricated for the affected limb 102 using a suitable manufacturing technique (e.g., additive manufacturing).

Two styles of orthosis have been identified depending on the age of the child. An orthosis with a static knee section may be used for patients aged between one and three years old, and an orthosis with a hinged-knee section may be used for patients aged between three and five.

Figure 2A:
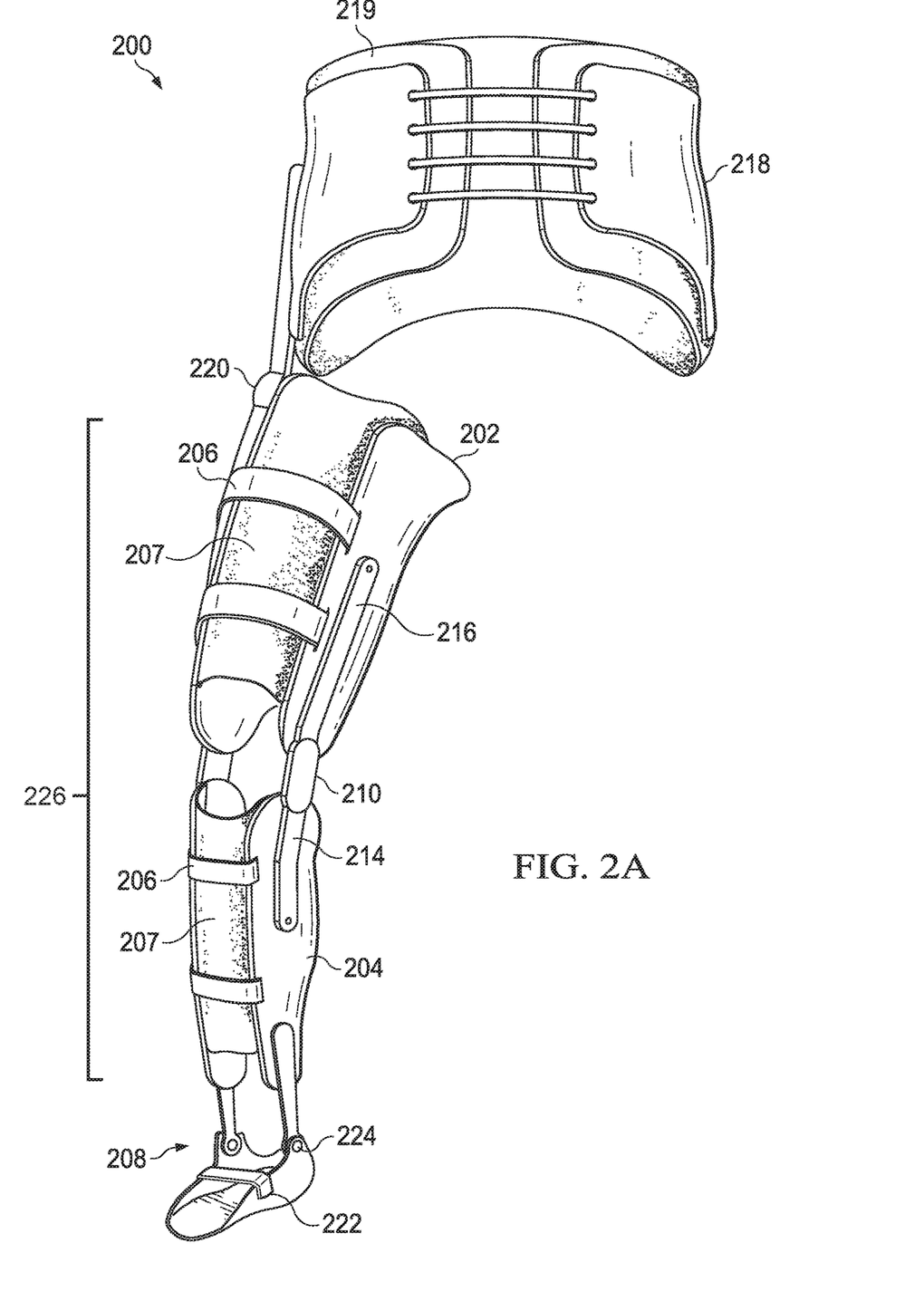
FIG. 2A is a schematic, perspective view of an embodiment of a femoral fracture brace.
Figure 2B:
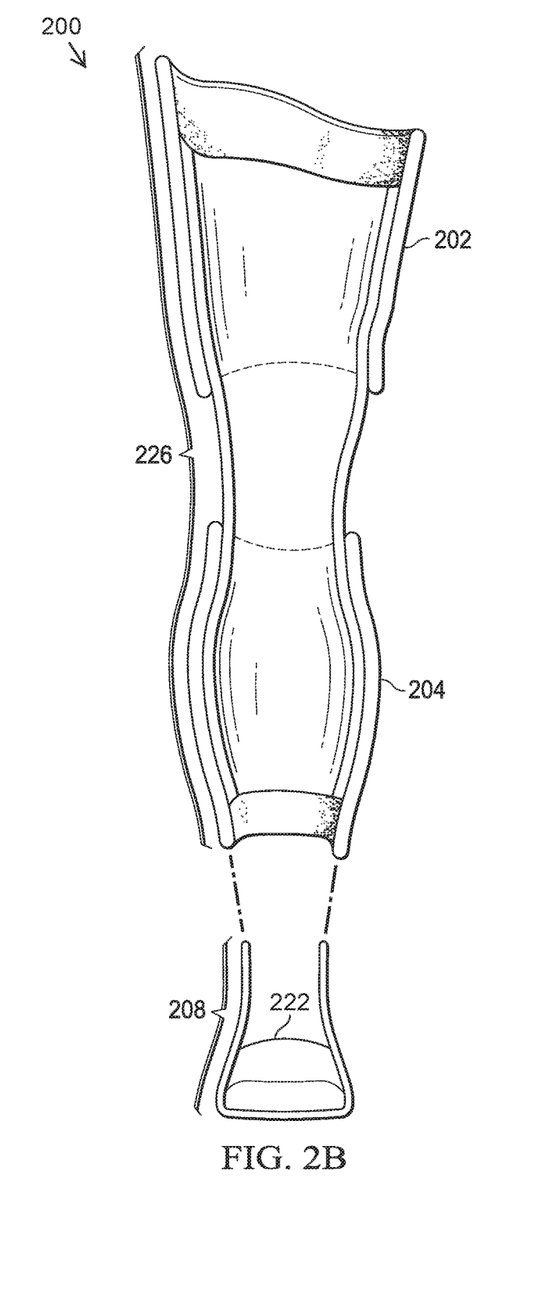
FIG. 2B is a schematic, front view of a portion of the femoral fracture brace of FIG. 2A.

As shown in FIGS. 2A and 2B, an orthosis 200 (i.e., a brace) with a static position of the knee flexion angle is fabricated for children aged between one and three years. The orthosis 200 includes a torso section 218, hip joint 220, leg section 226, and foot section 208.

In some embodiments, the torso section 218 is made from a rigid or semi-rigid, high-temperature plastic that encompasses the waist and hip levels of the patient's torso. The torso section 218 is covered by a removable soft interface 219 that can be cleaned as needed. The soft interface 219 isolates the plastic from the patient's skin. The torso section 218 maintains a stable, rigid base for the superior end of the orthosis 200 so that the patient cannot easily move to change the relative abduction/adduction angles at the hip joint, which can have deleterious effects on the alignment of the femur fracture. The soft interface 219 provides reduced pressure and less likelihood of skin irritations, over the bony anatomy of the torso. The soft interface 219 is easily accessible and removable in case of soiling.

The torso section 218 and leg section 226 are connected by a hip joint 220 which may be made from steel, such as stainless steel, a rigid plastic or resin, or a similar material. The hip joint 220 allows for adjustability of flexion/extension motions as well as abduction and adduction motions at the hip. The relatively rigid construction of the hip joint 220 provides stabilization so that the affected limb cannot vary from the abduction angle which is set at the initial fitting. The construction of the hip joint 220 allows for changing flexion/extension motions throughout the duration of treatment, as well as for changing the hip adduction/abduction angle during fitting. The ability to change the abduction angle allows a healthcare provider (e.g., a physician, nurse, or similar service provider) to re-align the affected limb if an x-ray or similar image shows that changing the alignment of the extremity at the hip would be beneficial for the alignment of the fractured femur. The hip joint 220 connects the torso section 218 of the orthosis 200 to the leg section 226 of the orthosis 200.

The hip joint 220 allows adjustability in both the sagittal and coronal planes, which enables a health care provider to change the abduction angle with a quick adjustment. This adjustment is comparable to cutting a wedge in a spica cast but is much faster and easier. The same adjustability exists for flexion and extension. Flexion can be locked out at any angle with the ability to change it to allow some motion, when deemed appropriate (e.g., for ease of sitting).

The leg section 226 is made from a different type of plastic compared to the torso section 218. The leg section 226 plastic is more flexible compared to that of the torso section 218 and has the ability to provide constant circumferential compression about the patient's leg when tightened to facilitate fracture healing and maintenance of fracture alignment.

The leg section 226 includes an upper leg section 202 and lower leg section 204. During fitting, the leg section 226 is set in a predetermined knee flexion angle by a fixed knee section 210. In some embodiments, the upper leg section 202 and lower leg section 204 may be formed as an integral, single unit with the knee section 210. In other embodiments, the knee section 210 may be joined to the upper leg section 202 by an upper connector 216 and to the lower leg section 204 by a lower connector 214. The upper leg section 202 partially surrounds the patient's upper leg from just above the knee joint to just below the perineum and encloses each side of the patient's upper leg and the rear of the patient's upper leg, leaving at least part of the front of the patient's leg exposed. The upper leg section 202 may enclose approximately 75% of the patient's upper leg. One or more panels 207 which may be thin, plastic anterior (front) panels, are added above the knee to enclose the leg and provide compressibility. The panels 207 may be fastened in place by straps 206. As such, the straps 206 may include a flexible component, such as a resilient material or web and hook strapping to provide variable compression about the patient's upper leg.

Similar to the upper leg section 202, the lower leg section 204 partially surrounds the patient's lower leg from just below the knee joint to just above the ankle, and encloses each side of the patient's lower leg and the rear of the patient's lower leg, leaving at least part of the front of the patient's lower leg exposed. The lower leg section 204 may enclose approximately 75% of the patient's lower leg. One or more panels 207, which may be thin, plastic anterior (front) panels, are added below the knee to enclose the lower leg and provide compressibility. As such, the straps 206 may include a flexible component, such as a resilient material or web-and-hook strapping, to provide variable compression about the patient's leg. The panels 207 may be fastened in place by straps 206. Ventilation holes may be placed in each of the upper leg section 202 and lower leg section 204 to provide ventilation to the patient's otherwise enclosed leg and mitigate or prevent skin irritation and potential infection.

The foot section 208 is a removable portion of the orthosis 200, and is attached to the lower leg section 204 by a hook-and-loop material (e.g., Velcro®) or similar fastener. The foot section 208 has an ankle hinge 224 that allows for free motion at the ankle and a strap 222 that goes over the instep of the foot which aids in holding the foot in to the foot section 208 of the brace. The plastic material utilized in the foot section 208 may be the same as or similar to the plastic utilized in the leg section 226.

Figure 3A:
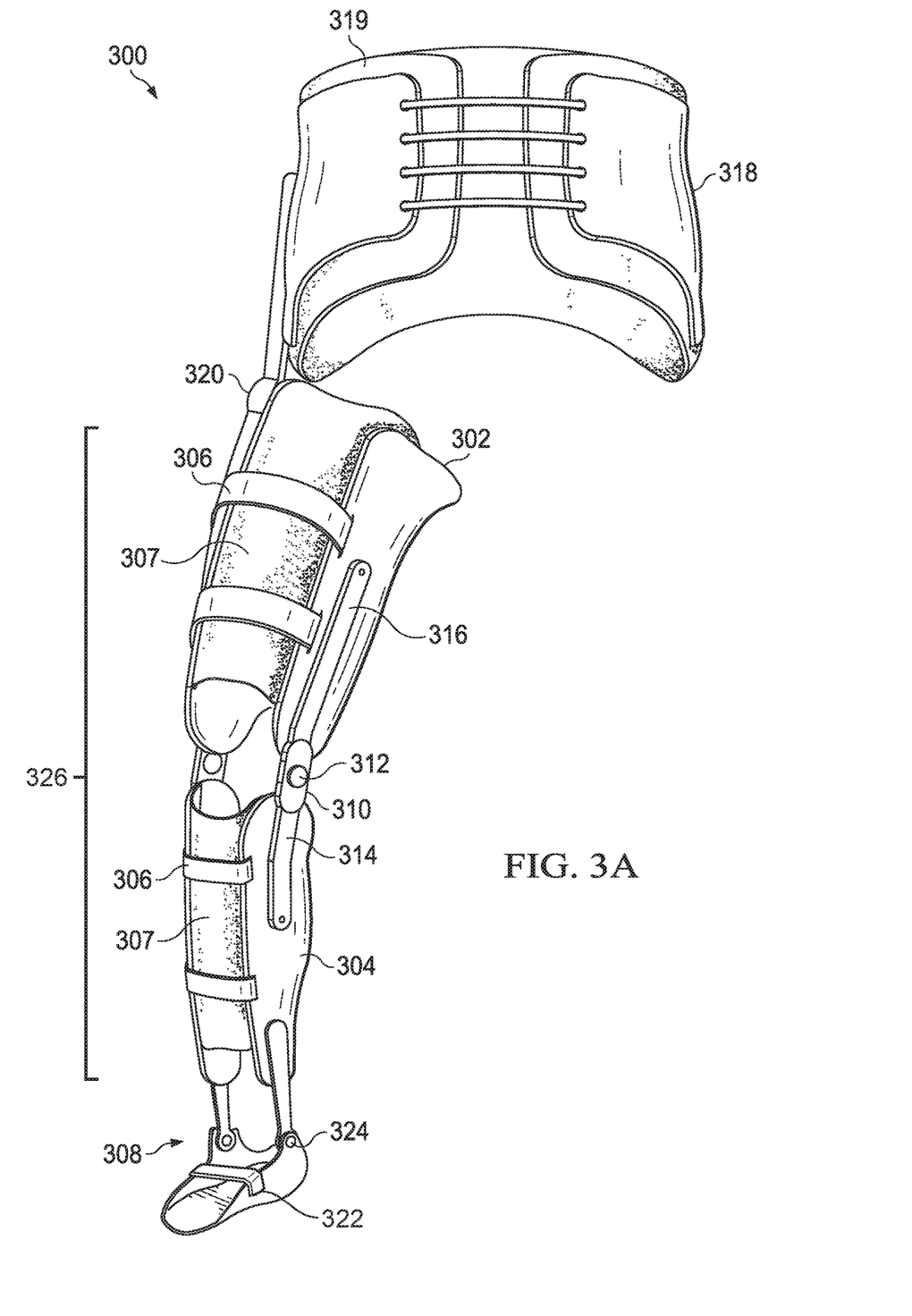
FIG. 3A is a schematic, perspective view of an alternative embodiment of a femoral fracture brace.
Figure 3B:
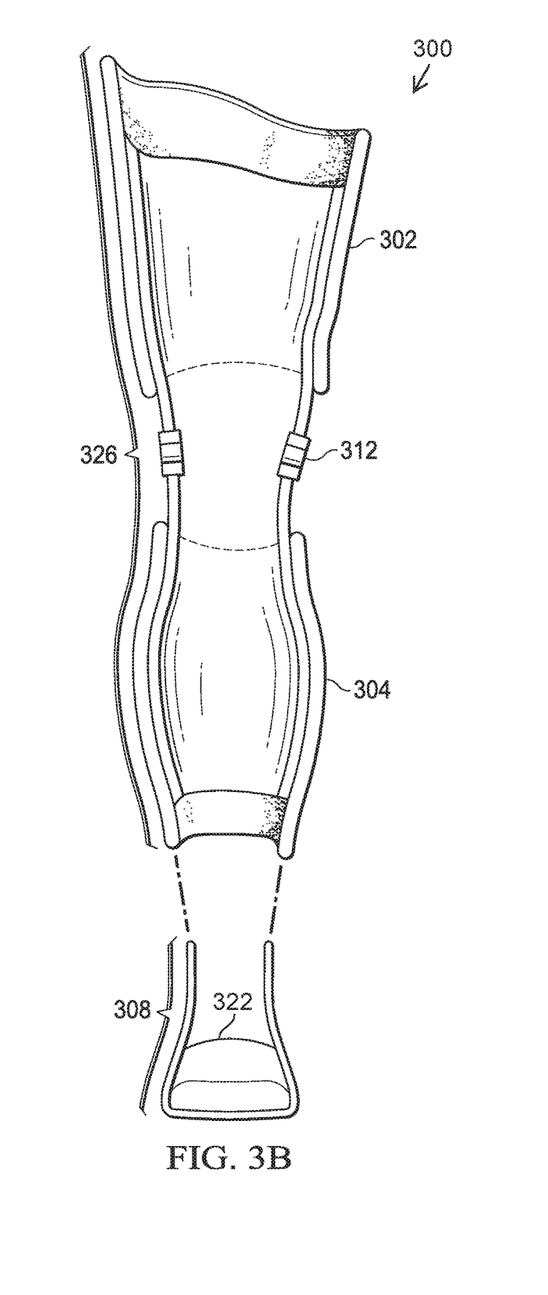
FIG. 3B is a schematic, front view of a portion of the femoral fracture brace of FIG. 3A.

As shown in FIGS. 3A and 3B, an orthosis 300 (i.e., a brace) with a flexible knee flexion angle is fabricated for children aged between three and five years. The orthosis 300 includes a torso section 318, hip joint 320, leg section 326, and foot section 308.

In some embodiments, the foot section 308 is a footplate with a free motion ankle joint 324 attached to the lower end of the lower leg section 304. The foot section 308 and ankle joint 324 may provide control of any rotary forces applied to the affected limb and also help to suspend the orthosis 300 when it is time for the patient to be in an upright position, whether weight bearing or not.

The torso section 318 is made from a rigid or semi-rigid, high temperature plastic that encompasses the waist and hip levels of the patient's torso. The torso section 318 is covered by a removable soft interface 319 that can be cleaned as needed. The soft interface 319 isolates the plastic from the patient's skin. The torso section 318 maintains a stable, rigid base for the superior end of the orthosis 300 so that the patient cannot easily move to change the relative abduction/adduction angles at the hip joint, which can have deleterious effects on the alignment of the femur fracture. The soft interface 319 provides reduced pressure and less likelihood of skin irritations over the bony anatomy of the torso. The soft interface 319 is easily accessible and removable in case of soiling.

The torso section 318 and leg section 326 are connected by a hip joint 320, which may be made from steel, such as stainless steel, a rigid plastic or resin, or a similar material. The hip joint 320 allows for adjustability of flexion/extension motions as well as abduction and adduction motions at the hip. The relatively rigid construction of the hip joint 320 provides stabilization so the affected limb cannot vary from the abduction angle which is set at the initial fitting. The construction of the hip joint 320 allows for changing flexion/extension motions throughout the duration of treatment as well as for changing the hip adduction/abduction angle during fitting. The ability to change the abduction angle allows a healthcare provider (e.g., a physician) to re-align the affected limb if an x-ray or similar image shows that changing the alignment of the extremity at the hip would be beneficial for the alignment of the fractured femur. The hip joint 320 connects the torso section 318 of the orthosis 300 to the leg section 326 of the orthosis 300.

The hip joint 320 allows adjustability in both the sagittal and coronal planes, which enables a healthcare provider to change the abduction angle with a quick adjustment. This adjustment is comparable to cutting a wedge in a spica cast but is much faster and easier. The same adjustability exists for flexion and extension. Flexion can be locked out at any angle with the ability to change it to allow some motion, when deemed appropriate (e.g., for ease of sitting).

The leg section 326 is made from a different type of plastic compared to the torso section 318. The leg section plastic is more flexible compared to that of the torso section 318 and has the ability to provide constant circumferential compression about the patient's leg when tightened to facilitate fracture healing and maintenance of fracture alignment.

The leg section 326 includes an upper leg section 302 and lower leg section 304. During fitting, the leg section 326 is set in a predetermined knee flexion angle by a hinged knee section 310. The hinged knee section 310 is joined to the upper leg section 302 by an upper connector 316 and to the lower leg section 304 by a lower connector 314. The hinge 312 allows for locking the knee at any angle, allowing motion within a defined range, or allowing completely free flexion and extension range of motion.

The upper leg section 302 partially surrounds the patient's upper leg from just above the knee joint to just below the perineum and encloses each side of the patient's upper leg and the rear of the patient's upper leg, leaving at least part of the front of the patient's leg exposed. The upper leg section 302 may enclose approximately 75% of the patient's upper leg. Panels 307, which may be thin, plastic anterior (front) panels, are added above the knee to enclose the leg and provide compressibility. The panels 307 may be fastened in place by straps 306. The straps 306 may include a flexible component, such as a resilient material or web-and-hook strapping, to provide variable compression about the patient's upper leg.

Similar to the upper leg section 302, the lower leg section 304 partially surrounds the patient's lower leg from just below the knee joint to just above the ankle, and encloses each side of the patient's lower leg and the rear of the patient's lower leg, leaving at least part of the front of the patient's lower leg exposed. The lower leg section 304 may enclose approximately 75% of the patient's lower leg. Panels 307, which may be thin, plastic anterior (front) panels are added below the knee to enclose the lower leg and provide compressibility. The panels 307 may be fastened in place by straps 306. Again, the straps 306 may include a flexible component, such as a resilient material or web-and-hook strapping, to provide variable compression about the patient's leg. Ventilation holes may be placed in each of the upper leg section 302 and lower leg section 304 to provide ventilation to the patient's otherwise enclosed leg and mitigate or prevent skin irritation and potential infection.

The upper leg section 302 and lower leg section 304 may be separate to allow the hinge settings to work. Relative movement between the separate upper leg section 302 and lower leg section 304, however, may not be optimal in the initial stages of immobilization. Thus, during the initial stages of immobilization, a thin, fixed transitional section may be inserted in place of the hinged knee portion 310 to provide immobilization of the lower leg relative to the upper leg. When knee motion is desired, the thin, fixed transitional section may be removed and replaced with the hinged knee portion 310 at the desired knee angle.

The foot section 308 is a removable portion of the orthosis 300, and is attached to the lower leg section 304 by a hook-and-loop material (e.g., Velcro®) or similar fastener. The foot section 308 has an ankle joint 324 that allows for free motion at the ankle and a strap 322 that goes over the instep of the foot which aids in securing the foot relative to the foot section 308 of the brace. The plastic material utilized in the foot section 308 may be the same as or similar to the plastic utilized in the leg section 326.

In some embodiments, the foot section 308 is a footplate with a free motion ankle joint 324 attached to the lower end of the lower leg section 304. The foot section 308 and ankle joint 324 may provide control of any rotary forces applied to the affected limb and also help to suspend the orthosis 300 when it is time for the patient to be in an upright position, whether weight bearing or not.

The material selections for each section of the orthosis 200 and orthosis 300 may vary according to the desired characteristics of each section. For example, the torso section 218/318 may be made out of a rigid thermoplastic that is operable to act as a stabilizing base to hold the patient's leg in desired positions in the coronal plane (abduction/adduction) and in the sagittal plane (flexion/extension). In some embodiments, the torso section 218/318 is well padded since it is a rigid plastic and will be anchored on the pelvis.

The leg section 226/326 may be made from a thin and flexible plastic that is meant to have some flexibility to provide constant compression over the fracture site. The selected materials accommodate fluctuating sizes of the thigh, mostly due to swelling and the subsequent reduction of swelling that may occur after compression is applied over the fracture.

The leg section 226/326 may not include a soft interface or liner, and may therefore be easier to keep clean and disinfected, while ventilation holes may be used to ensure that the area enclosed by the leg section 226/326 receives proper ventilation.

Straps 206/306 and panels 207/307 cover portions of the thigh and calf areas, and are attached in conjunction with flexible straps or other fasteners to provide desired compression. The anterior panels 207/307 may be separate "floating" pieces that slide inside of the upper leg sections 202/302 and lower leg sections 204/304 to provide the desired compression and allow the brace (orthosis 200/300) to act like a cast.

The flexibility of the upper leg section 202/302 and lower leg section 204/304 and the separate anterior panels 207/307 and straps 206/306 allow the orthosis 200/300 to maintain constant compression over the affected limb even as the size of the thigh changes with the degree of swelling. The plastic in the leg straps 206/306 also has ventilation holes to lessen the risk of skin irritations associated with heat and perspiration.

In accordance with the foregoing disclosure, an exemplary process for treating femoral fractures in children, the process comprising: (1) diagnosing a patient with a femoral shaft fracture of an affected limb; (2) enclosing the affected limb in a splint; (3) scanning the unaffected limb with a three-dimensional scanner; (4) measuring the unaffected limb to obtain brace measurements; (5) fabricating an orthosis to support the affected limb based on the scan of the unaffected limb; and (6) applying the orthosis to the affected limb.

The process may further include applying a stocking to the unaffected limb prior to scanning, and may include establishing landmarks on the unaffected limb (or on the stocking) prior to scanning. The landmarks may include one or more marks that are visible to a scanning apparatus, and may include at least one reference point. In some embodiments, the reference point is a mark placed at the front center of the knee of the patient's unaffected limb. Another landmark may be placed at the patient's perineum, and another landmark may be placed at the patient's ankle.

In some embodiments, measuring the unaffected limb includes taking circumferential measurements of the unaffected limb at preselected intervals along the unaffected limb. The circumferential measurements may be taken using a landmark at the center of the patient's knee as a reference point.

In some embodiments, the process includes generating a three-dimensional (virtual) model of the affected limb based on a scan of the unaffected limb. Generating the model may include applying a swelling factor to measurements of the unaffected limb and, more particularly, to those parts of the limb that are closest to the fracture.

In some embodiments, fabricating the orthosis includes fabricating an orthosis having a leg section and a torso section, wherein measurements used to fabricate the leg section and torso section are taken from the above-referenced model. The leg section may partially enclose a portion of the patient's affected limb.

In some embodiments, the orthosis includes a plurality of anterior panels that complement the leg section to enclose at least a portion of the patient's affected limb. The anterior panels may be held in place by compressive straps, and may also be fabricated using measurements or manufacturing parameters derived from the model.

In some embodiments, the leg section includes an upper leg section, a lower leg section, and a knee joint. Further, fabricating the orthosis may include fabricating a leg section (which may include an upper leg section and a lower leg section, and components thereof) and a torso section using an additive manufacturing technique.

The invention claimed is:

1. A process for treating femoral fractures in children, the process comprising:
   scanning an unaffected limb opposite an affected limb with a three-dimensional scanner to create a scan of the unaffected limb;
   measuring the unaffected limb to obtain brace measurements;
   fabricating an orthosis to support the affected limb based on the scanning and measuring of the unaffected limb; and
   generating a model of the affected limb based on a scan of the unaffected limb;
   wherein generating the model of the affected limb based on the scan of the unaffected limb comprises applying a swelling factor to measurements of the unaffected limb, and wherein applying the swelling factor to the measurements of the unaffected limb comprises applying a function of a distance from a fracture in the affected limb to the measurements of the unaffected limb.

\* \* \* \* \*